United States Patent [19]

Barr et al.

[11] Patent Number: 5,139,745
[45] Date of Patent: Aug. 18, 1992

[54] LUMINOMETER

[75] Inventors: Howard S. Barr, Escondido; Gregory E. Sancoff, Leucadia; Mark McWilliams, San Diego, all of Calif.

[73] Assignee: Block Medical, Inc., Carlsbad, Calif.

[21] Appl. No.: 503,682

[22] Filed: Mar. 30, 1990

[51] Int. Cl.$^5$ .................. G01N 21/01; G01N 21/66
[52] U.S. Cl. ................. 422/82.05; 250/361 C; 356/244; 356/440; 422/82.08; 436/172
[58] Field of Search ................ 356/244, 440; 250/361 C; 422/82.08, 82.05, 52; 436/172

[56] References Cited

U.S. PATENT DOCUMENTS

| | | | |
|---|---|---|---|
| 3,520,662 | 7/1970 | Chappelle et al. | 356/246 |
| 4,213,702 | 7/1980 | Haunold et al. | 356/244 |
| 4,730,933 | 3/1988 | Lohr | 356/244 |
| 4,772,453 | 8/1988 | Lisenbee | 422/52 |
| 4,818,883 | 4/1989 | Anderson et al. | 250/361 |

*Primary Examiner*—Jill A. Johnston
*Attorney, Agent, or Firm*—Baker, Maxham, Jester & Meador

[57] ABSTRACT

A luminometer for analyzing genetic or non-genetic maaterial comprises an optical chamber for receiving and holding a vial of the sample material in a dark environment. A pumping system mounted in the luminometer pumps reagents into the vial to cause the sample material to luminesce, and a sensor is positioned in the dark environment relative to the vial to detect the luminescence. Instantaneous intensities of the luminescence are sequentially sampled at set intervals of time during a preselected time period and summed by a microprocessor to generate a signal that is descriptive of the constituents of the sample.

18 Claims, 2 Drawing Sheets

LUMINOMETER

FIELD OF THE INVENTION

This invention pertains generally to diagnostic test equipment. More particularly, the present invention pertains to luminometers which can detect the luminescence from a sample material and generate a signal from the luminescence which is descriptive of constituent concentrations in the material. The present invention is particularly, but not exclusively, useful for determining the concentration of selected constituents in a genetic material.

BACKGROUND OF THE INVENTION

It is well known that various materials (including genetic materials) will luminesce under certain conditions and emit light at a wavelength with a variable intensity that is characteristic of the material. The nature of this so-called "light-off", however, is dependent on the particular assay which is used and the alacrity with which the assay is accomplished. Accordingly, by using precise timing in a procedure for a particular assay, the resulting luminescence from a sample material will give meaningful information about the concentration and constituency of the sample material.

In order for a sample material to luminesce and emit a light-off, the material is exposed to specific reagents according to a selected assay. After exposure of the material to these reagents, an increase in luminescence results from whatever steady state luminescence may be inherent in the material. Typically, this increased luminescence is characterized by a relatively rapid rise in the intensity of the light that is emitted from the sample. This rise is then immediately followed by a relatively slower return to ambient light intensity. Thus, emission intensity is typically represented by a curve having a skewed peak. For most materials, such a light-off occurs within a time period of approximately two (2) seconds.

To ascertain meaningful information about the sample material, it has been necessary for prior art luminometers to count photons and continuously integrate the intensity of the luminescence over a period of time to obtain a value which could be used for quantifying the sample. Since the light-offs obtained by perviously used assays were of particularly low intensity, and consequently difficult to read, the earlier luminometers necessarily incorporated high-cost precision components in order to detect this luminescence.

It has happened that improved assays are now giving better, and hence more readable, light-offs. Also, under certain circumstances, even the steady state luminescence after the light-off can be useful for analysis. As a consequence, the more sophisticated equipment which was required in the past to accurately record and profile a light-off for diagnostic purposes can now be replaced by less sophisticated equipment. Indeed, the present invention recognizes this can be done without any meaningful loss in the quality of the assay results.

In light of the above, it is an object of the present invention to provide a luminometer which can accurately sample the luminescence from a sample material for diagnostic purposes. Yet another object of the present invention is to provide a luminometer which can refine assay results by excluding background light from the luminescent signal that is descriptive of a sample's constituent concentration. Still another object of the present invention is to provide a luminometer that can be used for different assays. Finally, it is an object of the present invention to provide a luminometer which is relatively easy to use and comparatively cost-effective.

SUMMARY OF THE INVENTION

A luminometer for analyzing material includes an instrument which has an optical chamber that can receive a vial containing the material to be tested and hold it in a very dark environment. Specifically, the optical chamber of the luminometer is a hollow cylindrical-shaped tube having a closed end and having an open end through which the vial can be inserted. A light shield is positionable over the vial and across the open end of the optical chamber to create the dark environment necessary for operation of the luminometer. Once the light shield has been properly positioned over the open end of the optical chamber, a probe is activated to drive the vial farther into the chamber and position the vial with its contents exposed to a window that is formed in the side wall of the optical chamber. As intended for the present invention, a spring loaded shutter is slidably disposed within the optical chamber and is positioned across the window when the shutter and spring are in equilibrium. When the vial is inserted into the optical chamber, the base of the vial rests against the shutter. Thus, as the probe drives the vial into the optical chamber, it also drives the shutter against the spring to move the shutter and open the window.

A light sensor, which is preferably a photomultiplier tube, is positioned externally against the optical chamber to establish a light path between the sensor and the contents in the vial when the window is open. To preserve the dark environment, the sensor is completely encased so there can be no light access to the sensor except through the window. A microprocessor is electrically connected to the sensor and is used to process data received by the sensor for indicating the constituents of the material held in the vial.

A pumping system is provided for the luminometer which pumps appropriate reagents at predetermined times through the probe and into the vial in its dark environment to initiate luminescense of the sample material. As intended for the present invention, the sensor detects this luminescense and the microprocessor uses the resultant data to generate a signal that is descriptive of the vial's contents.

In the operation of the present invention, a vial containing the material to be sampled is placed into the optical chamber of the luminometer. With the light shield positioned over the open end of the chamber, the probe is urged against the vial to move the shutter into the chamber and thereby open the window and position the vial in the opened window. Reagents are then pumped into the vial in accordance with a prescribed assay to cause the material in the vial to luminesce.

As indicated above, the sensor detects the luminescence from the sample. More specifically, instantaneous intensities of the luminescence are sampled by the microprocessor at set intervals during a preselected time period. For example, the instantaneous intensity of the luminescence is determined approximately every one thirtieth (1/30) of a second over a two (2) second time period. With these instantaneous intensities, a profile sum of the luminescence can be determined which is characteristic of the sample material. Thus, as intended for the present invention, a sum of all instantaneous intensity readings during the preselected time period is calculated and used to generate a signal which is descriptive of the sample's constituents. A refinement of this descriptive signal can be made by subtracting a background signal from the sum of instantaneous intensity readings which is obtained during the preselected time period. Specifically, with the vial in position across the window and the optical channel sealed to establish the dark environment, light readings can be made by the sensor for a selected time period (e.g. one (1) second) to determine a background signal. Of necessity, this background signal is determined during a time interval that is prior to initiation of the luminescence.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
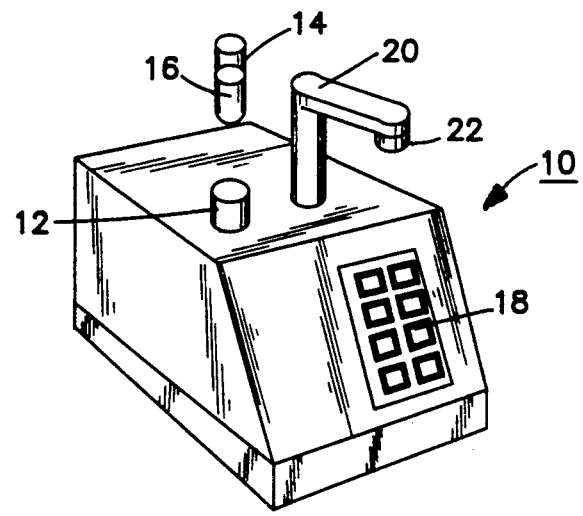
FIG. 1 is a perspective view of the luminometer of the present invention.

Referring initially to FIG. 1, a luminometer according to the present invention is shown and generally designated 10. As shown, luminometer 10 has an optical chamber 12 for receiving and holding a vial 14 which contains a material 16 to be sampled. The luminometer 10 also has a key pad 18 which can be used by an operator to program the luminometer 10 for its operation. Additionally, luminometer 10 has a tower 20 which can be swung clear of optical chamber 12 (as shown in FIG. 1) to permit insertion of vial 14 into the chamber 12. As intended for the present invention, after vial 14 has been inserted into optical chamber 12, tower 20 can be swung into position with the probe 22 that is mounted on tower 20 over vial 14 to operationally engage probe 22 with vial 14.

Figure 2:
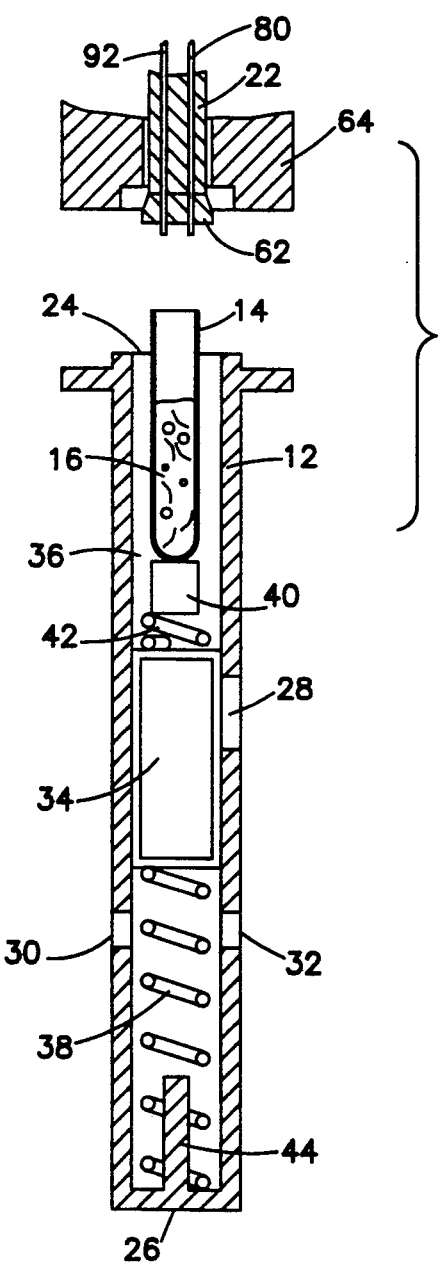
FIG. 2 is a cross-sectional schematic of the optical chamber with the light shield and reagent probe disengaged.

As is to be appreciated by reference to the schematic drawing in FIG. 2, optical chamber 12 is preferably a hollow cylindrical-shaped tube having an open end 24 and a closed end 26. Formed into the side wall of optical chamber 12 is a window 28 and a pair of diametrically opposed light ports 30 and 32. A cylindrical shutter 34 is slidably disposed within the cavity 36 of optical chamber 12 and rests on a spring 38 which positions shutter 34 across window 28 when the shutter 34 and spring 38 are in equilibrium. Effectively, this allows shutter 34 to prevent the passage of light through window 28. A spacer 40 rides in cavity 36 above the shutter 34 and is separated therefrom by a spring 42. For purposes of the present invention, the spring constant for spring 42 is sufficiently lower than the spring constant for spring 38. Accordingly, in response to the movement of vial 14 into cavity 36 of optical channel 12, spacer 40 urges against shutter 34 before there is any significant yielding by spring 38 to allow the movement of shutter 34 which will open window 28.

FIG. 2 also shows a shutter stop 44 affixed within cavity 36 to the closed end 26 of optical channel 12. A purpose of shutter stop 44 is to limit the distance shutter 34, and consequently vial 14, can be moved into optical channel 36. Such a limit is needed in order to properly position vial 14 relative to window 28 for the operation of luminometer 10 disclosed below and to prevent fouling of spring 38. Additionally, FIG. 2 indicates that an annular flange 46 surrounds open end 24 of optical chamber 12 substantially as shown.

Figure 3:
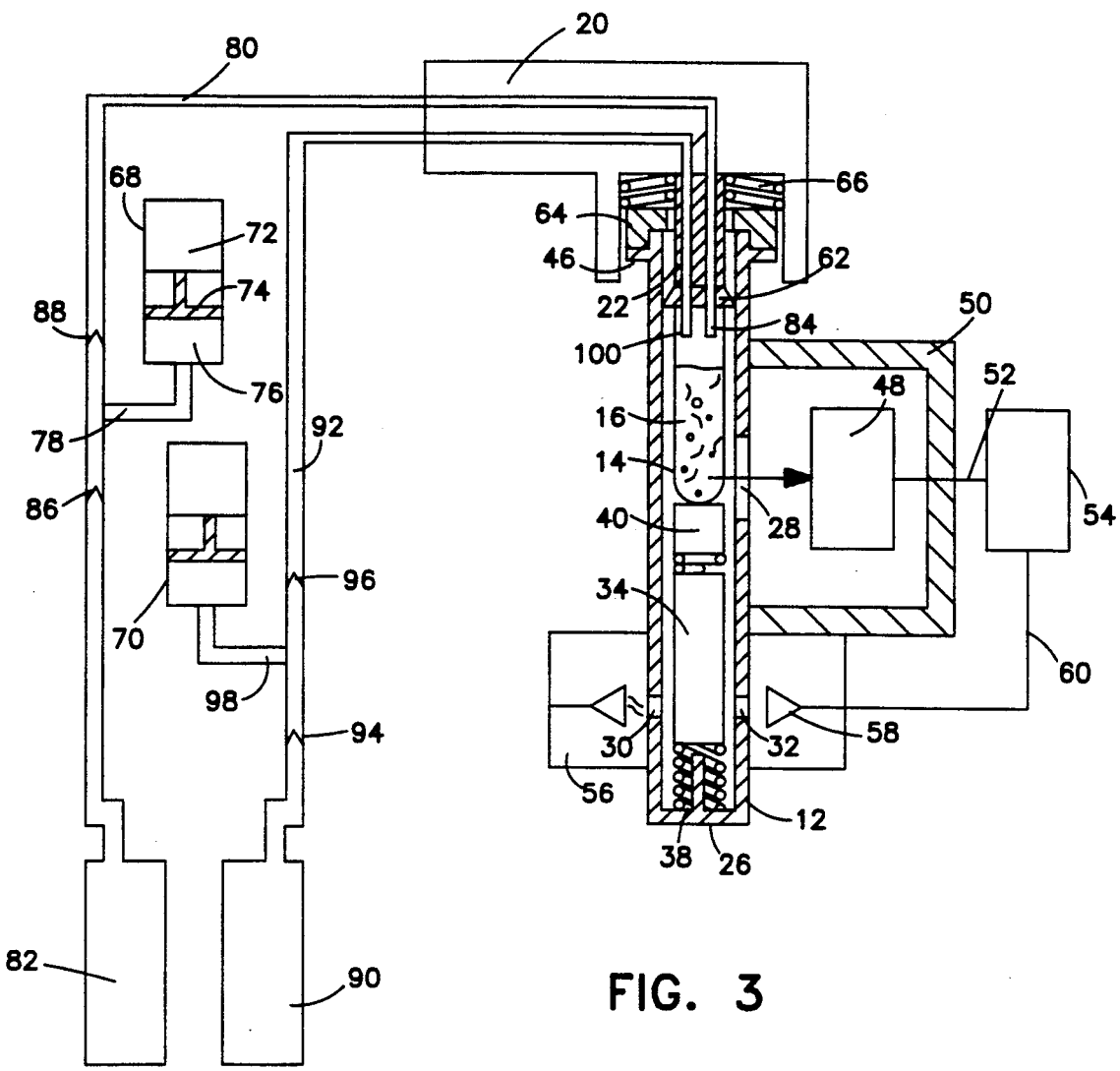
FIG. 3 is a cross-sectional schematic of the optical chamber and associated components with the light shield and reagent probe engaged with the optical chamber.

The structural interaction of optical chamber 12 with other components of luminometer 10 can perhaps be best seen with reference to FIG. 3. In FIG. 3, it can be seen that a sensor 48 is mounted and encased in a housing 50 which is attached to the outside of optical chamber 12. Importantly, sensor 48 is positioned so that a light pathway exists through window 28 between sensor 48 and the material 16 in vial 14 when the insertion of vial 14 into optical chamber 12 has caused shutter 34 to move and open window 28. Preferably, sensor 48 is a combination of a photomultiplier tube and transimpedence amplifier. The photomultiplier tube is preferably of a type commercially sold by Hammamatsu and the transimpedence amplifier is an augmented amplifier of a type commercially sold by Burr-Brown. As further indicated in FIG. 3, sensor 48 is electrically connected via line 52 to a microprocessor 54. Microprocessor 54 can be of any commercially available type that is well known in the art. Preferably, however, microprocessor 54 is a Motorola 68HC11F1-FN, microcontroller.

In order to indicate when shutter 34 has been moved to open window 28, a light source 56 (e.g. a light emitting diode) is attached to optical channel 12 to direct light through light port 30. If shutter 34 has not been moved to open window 28, light from the source 56 will pass through both light port 30 and light port 32 and be received by a light detector 58 (e.g. a phototransistor). On the other hand, shutter 34 will block light from source 56 to detector 58 when vial 14 has been inserted into optical channel 12 to move shutter 34. Thus, when light is received by light detector 58, a signal can be sent to microprocessor 54 via an electrical connection 60 to indicate window 28 is not open and vial 14 is not in place. On the other hand, when no light is received by light detector 58, microprocessor 54 will operate with information that window 28 is open and that vial 14 is in place.

The interaction between tower 20 and optical chamber 12 which results in the operative engagement of probe 22 with vial 14 can be best appreciated by cross referencing FIG. 2 with FIG. 3. Specifically, in both FIGS. 2 and 3, it can be seen that the probe 22 is formed with a lip 62 which is engageable with vial 14 to urge the vial 14 into a position in optical chamber 12 as shown in FIG. 3. Additionally, a light shield 64 slidingly surrounds probe 22 and is restingly engageable with flange 46 to create a dark environment within optical chamber 12 and the housing 50 when vial 14 is positioned as shown in FIG. 3. Specifically, as will be appreciated by cross referencing the configuration of probe 22 and light shield 64 in FIG. 2 with that shown in FIG. 3, when tower 20 is lowered over optical channel 12 to engage probe 22 with vial 14, the spring 66 in tower 20 is compressed to urge light shield 64 against flange 46. Simultaneously, probe 22 urges against vial 14 to compress spring 42 and cause spacer 40 to contact shutter 34. At this point, light shield 64 engages flange 46. Additional movement of probe 22 into optical chamber 12 causes shutter 34 to open window 28 and position the material 16 held in vial 14 for light communication with the sensor 48 as shown in FIG. 3. For purposes of the present invention, the dark environment in optical chamber 12 is preferably on the order of approximately one million photons per sec-cm$^2$ (1,000,000 photons/sec-cm$^2$).

FIG. 3 also shows that luminometer 10 has a parallel pumping system which includes a pump 68 and a pump 70. Preferably, both pumps 68 and 70 may be any of the well known syringe pumps which can deliver precise quantities of fluid at a desired rate of fluid flow. More specifically, pump 68 includes a drive unit 72 which reciprocates a plunger 74 within the fluid chamber 76 of pump 68. It is to be appreciated that pumps 68 and 70 may also be Bellows pumps. In either case, the outlet 78 of pump 68 is in fluid communication with a fluid line 80 that connects a fluid source 82 in fluid communication with the nozzle 84 which is mounted in probe 22. As shown, fluid line 80 also has a one-way valve 86 which is located between fluid source 82 and the outlet 78 of pump 68, and a one-way valve 88 which is located between the outlet 78 and nozzle 84. As will be appreciated by the skilled artisan, one-way valves 86, 88 may be of any type well known in the art and are respectively located in fluid line 80 to insure fluid is pumped from fluid source 82 toward nozzle 84 and not in the reverse direction. Fluid pump 70 is similar in all important respects to pump 68 and is used, similarly to pump 70, for pumping fluid from a fluid source 90 into fluid line 92 and to nozzle 100 through a pair of one-way valves 94, 96 which straddle the outlet 98 of pump 70. For purposes of the present invention, the various components and pumps are selected to minimize contamination of reagent fluids.

OPERATION

To begin, the material 16 to be analyzed is placed in vial 14. This material 16 may be genetic material. The vial 14 is then placed into optical chamber 12 and is positioned therein as substantially shown in FIG. 2. With vial 14 in chamber 12, tower 20 is rotated into position with probe 22 poised above vial 14. Tower 20 is initially lowered to engage lip 62 of probe 22 with vial 14. Tower 20 is then further lowered until light shield 64 contacts flange 46 in order to establish a dark environment within chamber 12 and housing 50. This action also causes spacer 40 to urge against shutter 34. Still further lowering of tower 20 leaves light shield 64 in surrounding contact with flange 46 and causes probe 22 to push vial 14 into the position shown in FIG. 3.

With vial 14 in the dark environment of optical chamber 12, reagents from fluid sources 82, 90 are respectively pumped via fluid lines 80, 92 into vial 14 according to a predetermined assay. What these reagents do for the actual operation of luminometer 10 will perhaps be best appreciated by reference to FIG. 4.

Figure 4:
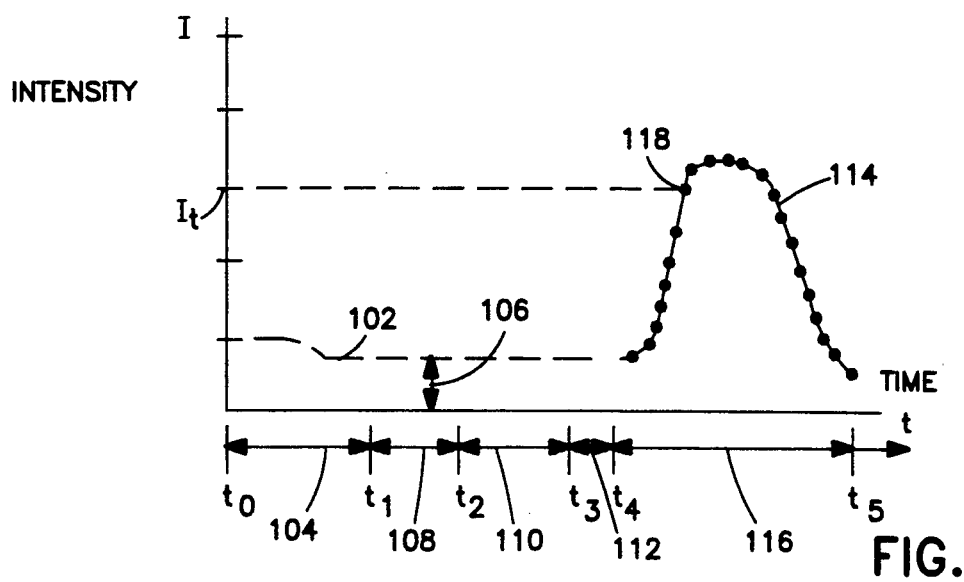
FIG. 4 is a graph indicating the luminescence of a sample material over time, and a time sequence of the procedure for describing the luminescence.

Referring to FIG. 4 a typical operation for luminometer 10 is depicted in terms of a graph which plots light intensity (I) within optical chamber 12 (as detected by sensor 48) against time (t). As shown in FIG. 4, an operational cycle for luminometer 10 begins at $t_0$. As intended for the present invention, $t_0$ is triggered by a switch (not shown) which is activated when tower 20 is lowered and vial 14 is in place across window 28. For example, $t_0$ can occur when shutter 34 interrupts light from light source 56 to send a signal from light detectors 58 to microprocessor 54 via connection 60. On the other hand, even if tower 20 is lowered, unless shutter 34 interrupts light from light source 56, there can be no operation. This precludes pumping reagent fluid into an empty optical chamber 12.

Immediately subsequent to $t_0$ the ambient intensity detected by sensor 48 (as indicated by the dashed line 102) will vary somewhat during a warm-up period 104 for sensor 48. Specifically, warm-up period 104 extends from $t_0$ to $t_1$ and will typically last approximately nine (9) seconds. During this warm-up period 104, sensor 48, which is initially energized at a stand-by voltage of approximately four hundred and seventy (470) volts, is activated to an operational voltage that is approximately twice the magnitude of the stand-by voltage, i.e. nine hundred and forty (940) volts. Two operational features should be noted here. First, the fact that sensor 48 is initially energized reduces the length of warm-up period 104. Second, electronic componentry can be incorporated which will prevent the higher voltage on sensor 48 when tower 20 is up and not engaged with optical chamber 12.

Immediately following warm-up period 104, a background signal 106 is determined which represents the ambient light intensity within the dark environment of optical chamber 12. As shown in FIG. 4, background signal 106 is determined during a sampling period 108 which extends from $t_1$ to $t_2$. Typically, sampling period 108 lasts approximately one (1) second and allows for approximately thirty-two (32) discrete intensity samples to be taken. These discrete intensity samples are then averaged by microprocessor 54 to establish the magnitude of background signal 106. It can be noted that, rather than waiting a full nine (9) seconds for warm-up period 104 to begin, $t_1$ may occur as soon as it has been determined the ambient intensity within the dark environment is substantially constant. Thus, as soon as sensor 48 and associated microprocessor 54 detect a consecutive sequence of substantially equal light intensity samples, sampling period 108 can begin (i.e. $t_1$ occurs). For purposes of the present invention, whenever five (5) intensity samples are substantially equal to each other, it is possible to consider that a background signal 106 is determinable and $t_1$ can be marked.

After background signal 106 is established, a first reagent held in fluid source 82 can be pumped into vial 14 during the time period 110 in accordance with the particular assay being used. Time period 110 extends from $t_2$ to $t_3$ and will typically be on the order of two (2) seconds. This is followed by an approximately one (1) second delay period 112 from $t_3$ to $t_4$ which immediately precedes the pumping of a second reagent from fluid source 90 into vial 14 at $t_4$.

Approximately between two tenths and three tenths (0.2–0.3) of a second after $t_4$, the material 16 in vial 14 will begin to "light-off". This "light-off" is characterized by a rapid increase in light intensity within the optical chamber 12 as indicated by the curve 114 in FIG. 4. After curve 14 peaks, there is a more gradual decrease in the light intensity detected by sensor 48 until the curve 114 again indicates that light intensity within the dark environment of optical chamber 12 has returned to a level which is represented by background signal 106. Effectively, as shown in FIG. 4, curve 114 (i.e. the light-off) is generated during a programmable period 116 which extends from $t_4$ to $t_5$. Normally the light-off will occur within a programmable period 116 which is approximately two (2) seconds in duration. During this period 116, however long it may be, sensor 48 detects light intensity within the optical chamber 12. Specifically, the instantaneous intensity of light within chamber 12 during programmable period 116 is sampled approximately thirty (30) times each second and a signal indicating each instantaneous intensity is electrically transmitted to microprocessor 54. For example, the instantaneous intensity ($I_t$) represented by point 118 on curve 114 is but one of thirty such signals sent each second to microprocessor 54 during the programmable period 116.

As will be readily appreciated by the skilled artisan, the luminescence from material 16 which is represented by curve 114 is characteristic of the material 16. More specifically, the area under curve 114 is indicative of the concentration of certain constituents in the material 16. Thus, by using well known electronic circuitry in microprocessor 54 to sum all of the instantaneous intensities (i.e. transient instantaneous intensity 118 et al.) during programmable period 116, a descriptive signal can be generated which gives the concentration of certain constituents in material 16. This descriptive signal can be refined to be made more precise by subtracting background signal 106 therefrom. It is also to be appreciated that the preselected time period for the programmable period 116 used to detect instantaneous intensities can be established after the light-off. Accordingly, a descriptive signal can include the sum of instantaneous intensities which are detected after luminescence from material 16 has attained a steady state level. In either case, in accordance with the present invention, the descriptive signal can be used by electronic means well known in the art to indicate a positive sample, e.g. a constituent concentration above some predetermined "cut off" level for the particular sample. Further, means can be employed to generate an alarm when the light intensity, and hence the concentration of certain constituents within material 16, rises above a predetermined level.

In light of the above, it will be understood that the steady state luminescence of an inherently luminescent material can be detected by the luminometer 10 of the present invention. To do so, the background signal would be determined from an empty dark environment within the optical chamber 12. Then, the material to be analyzed can be placed in vial 14 and inserted into optical chamber 12 for the determination of its steady state luminescence by sensor 48.

While the particular luminometer as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. An apparatus for analyzing the constituents of a sample held in a vial which comprises:
    means for holding said vial containing said constituents in a dark environment;
    means for sensing luminescence from said constituents in said dark environment;
    means electrically connected with said sensing means for determining instantaneous intensities of said luminescence at a plurality of set intervals of less than one second during a preselected time period; and
    means electrically connected with said determining means for summing a sufficient number of said instantaneous intensities within said time period for determining total luminescence from said constituents and for generating a descriptive signal indicative of the constituents of said sample.

2. An apparatus for analyzing the constituents of a sample held in a vial as recited in claim 1 wherein said holding means is a tubular-shaped optical chamber for receiving said vial, said chamber having a window for establishing a light path between said vial and said sensing means.

3. An apparatus for analyzing the constituents of a sample held in a vial as recited in claim 1 wherein said sensing means is a photomultiplier tube.

4. An apparatus for analyzing the constituents of a sample held in a vial as recited in claim 1 further comprising a pumping system for injecting reagents into said vial to cause said sample to luminesce.

5. An apparatus for analyzing the constituents of a sample held in a vial as recited in claim 4 wherein said pumping system comprises a first pump for injecting a reagent into said vial to prepare said sample and a second pump for subsequently injecting a reagent into said vial to initiate said luminescence.

6. An apparatus for analyzing the constituents of a sample held in a vial as recited in claim 1 wherein said determining means determines a steady state background signal indicative of light in said chamber when said sample does not significantly luminesce.

7. An apparatus for analyzing the constituents of a sample held in a vial as recited in claim 6 wherein said summing means subtracts said background signal from the sum of said instantaneous intensities to generate said descriptive signal.

8. An apparatus for analyzing the constituents of a sample held in a vial as recited in claim 7 wherein said determining means further comprises sampling means for periodically sampling light in said chamber to generate sample signals and begin determination of said background signal when consecutive sample signals are substantially equal.

9. A luminometer for analyzing the constituents of a sample of material held in a transparent vial which comprises:
    an optical chamber for receiving and holding said vial in a dark environment;
    a sensor positioned relative to said chamber for sensing luminescence from said sample;
    a detector electrically connected with said sensor for determining a substantially constant background signal and a plurality of intensity signals, said intensity signals corresponding to the instantaneous intensity of said luminescence at set intervals of less than one second during a preselected time period; and
    a summer for adding a sufficient number of said plurality of intensity signals within said time period and subtracting said background signal therefrom for determining total luminescence from said sample and for generating a descriptive signal indicating the constituents of said sample.

10. A luminometer for analyzing the constituents of a sample of material held in a transparent vial as recited in claim 9 wherein said optical chamber is tubular-shaped and has a window for establishing a light path between said vial and said sensor.

11. A luminometer for analyzing the constituents of a sample of material held in a transparent vial as recited in claim 9 wherein said sensing means is a photomultiplier tube.

12. A luminometer for analyzing the constituents of a sample of material held in a transparent vial as recited in claim 9 further comprising a pumping system for injecting reagents into said vial to cause said sample to luminesce.

13. A luminometer for analyzing the constituents of a sample of material held in a transparent vial as recited in claim 12 wherein said pumping system comprises a first pump for injecting a reagent into said vial to prepare said sample and a second pump for subsequently injecting a reagent into said vial to initiate said luminescence.

14. A luminometer for analyzing the constituents of a sample of material held in a transparent vial as recited in claim 9 wherein said determining means further comprises sampling means for periodically sampling light in said chamber to generate sample signals and begin determination of said background signal when consecutive sample signals are substantially equal.

15. A luminometer for analyzing the constituents of a sample of material held in a transparent vial as recited in claim 9 further comprising a shutter disposed in said chamber for normally covering said window, said shutter being displaceable by a vial placed in said chamber for exposing said window to light from the interior of said chamber.

16. A luminometer for analyzing the constituents of a sample of material held in a transparent vial which comprises:
  an optical chamber for receiving and holding said vial in a dark environment;
  a window in a wall of said chamber and a shutter disposed in said chamber for normally covering said window, said shutter being displaceable by a vial placed in said chamber for exposing said window to light from the interior of said chamber;
  a detector for detecting the displacement of said shutter from said window for indicating the presence of a vial in said chamber and generating and sending an initiation signal for initiating an operational cycle;
  a sensor positioned relative to said chamber for sensing luminescence from said sample;
  a detector electrically connected to said sensor for determining a substantially constant background signal and a plurality of intensity signals corresponding to the instantaneous intensity of said luminenscence at set intervals during a preselected time period; and
  a summer for adding said plurality of intensity signals and subtracting said background signal therefrom to generate a descriptive signal indicating the constituents of said sample.

17. A luminometer for analyzing the constituents of a sample of material held in a transparent vial which comprises:
  a substantially cylindrical optical chamber for receiving and holding a vial in a dark environment;
  a photo multiplier tube positioned relative to said chamber for sensing light from said chamber and generating a light intensity signal in response thereto;
  a window disposed in a sidewall of said optical chamber for establishing a light path between said chamber and said photo multiplier tube;
  a shutter disposed in said chamber for normally covering said window, said shutter being displaceable by a vial placed in said chamber for exposing said window to light in the interior of said chamber;
  a detector for detecting the displacement of said shutter from said window and generating an operational signal in response thereto;
  a pumping system for injecting reagents into said vial for causing said sample to luminesce; and
  operating means including microprocessor means electrically connected with said photo multiplier tube for receiving said light intensity signal for periodically sampling light in said chamber for a first period of time in response to an operational signal after a vial containing a sample is inserted in said chamber for determination of when consecutive sample signals are substantially equal for determining a substantially constant background signal, and for receiving a plurality of intensity signals over a second period of time following the injection of reagents into said vial, said intensity signals corresponding to the instantaneous intensity of said luminescence at set intervals of approximately one-thirtieth of a second during a preselected time period of approximately two-seconds, said operating means operative for adding said plurality of intensity signals and subtracting said background signal therefrom for generating a descriptive signal indicating the constituents of said sample.

18. A luminometer for analyzing the constituents of a sample of material held in a transparent vial as recited in claim 17 wherein said pumping system comprises a first pump for injecting a reagent into said vial to prepare said sample and a second pump for subsequently injecting a reagent into said vial to initiate said luminescence.

* * * * *